United States Patent [19]

Grossman et al.

[11] Patent Number: 5,026,888
[45] Date of Patent: Jun. 25, 1991

[54] RUTHENIUM TEREPHTHALATE

[75] Inventors: Richard F. Grossman, Shelton, Conn.; David M. Tanno, Richmond Heights, Ohio

[73] Assignee: Synthetic Products Company, Cleveland, Ohio

[21] Appl. No.: 356,638

[22] Filed: May 24, 1989

Related U.S. Application Data

[63] Continuation of Ser. No. 224,828, Jul. 27, 1988, abandoned.

[51] Int. Cl.$^5$ .............................................. C07F 15/00
[52] U.S. Cl. .................................................. 556/136
[58] Field of Search .................... 556/136; 437/1, 196, 437/201

[56] References Cited

U.S. PATENT DOCUMENTS

| | | | |
|---|---|---|---|
| 2,280,474 | 4/1942 | Byrkit et al. | 556/106 |
| 2,355,240 | 8/1944 | Reiff | 556/136 |
| 3,314,919 | 4/1967 | Most | 260/45.85 |
| 3,674,894 | 7/1972 | Economy et al. | 260/875 |
| 3,754,986 | 8/1973 | Perez-Albuerne | 437/1 X |
| 3,884,825 | 5/1975 | Lindblad et al. | 252/62.1 |
| 3,973,982 | 8/1976 | Bingham | 106/298 |
| 4,039,515 | 8/1977 | Rebhan et al. | 260/75 |
| 4,096,109 | 6/1978 | Watanabe | 260/40 |
| 4,101,523 | 7/1978 | Watanabe | 528/309 |
| 4,198,458 | 4/1980 | Mitsuishi | 428/212 |

OTHER PUBLICATIONS

Svoboda et al., "Ruthenium Carboxylates Bonded to Polyester", Chem. Abstracts, 96(16); 123559d.

*Primary Examiner*—Arthur C. Prescott
*Attorney, Agent, or Firm*—Wood, Herron & Evans

[57] ABSTRACT

Ruthenium terephthalate has been prepared and has been found to be especially suitable as a semiconductor.

1 Claim, No Drawings

RUTHENIUM TEREPHTHALATE

This application is a continuation of application Ser. No. 224,828, filed July 27, 1988.

BACKGROUND OF THE INVENTION

Numerous metal salts of terephthalic acid have been reported in the literature with a broad range of utilities, most often as additives to polymeric compositions. For example, in U.S. Pat. No. 3,314,919 terephthalates of calcium, barium, manganese, zinc and cadmium were reportedly prepared and incorporated into textile fibers for the improvement of mechanical properties of such fibers. Other examples of patent literature disclosing metal terephthalates, principally in polymeric compositions, include U.S. Pat. Nos. 3,674,894; 3,884,825; 3,973,982; 4,039,515; 4,096,109; 4,101,523; 4,198,458 and others. Other literature has reported upon metal terephthalates and study of their various properties, but delineation of details of such studies are not considered to be relevant to the subject matter of this invention.

SUMMARY OF THE INVENTION

This invention is directed to a new metal salt of terephthalic acid, specifically ruthenium terephthalate. Ruthenium terephthalate has been prepared and it has been found that this compound has an unusually high dielectric constant. Moreover, the compound has been found to have a very low volume resistivity of about $10^2$ or $10^3$ ohm-cm that makes it especially suitable for use as a semiconductor.

DETAILED DESCRIPTION

A. Preparation of Ruthenium Terephthalate

A stoichiometric excess of terephthalic acid was dissolved in 10% sodium hydroxide aqueous solution. To this solution was added 10 grams of ruthenium trichloride dissolved in 100 mls water, resulting in a black precipitate. The precipitate was filtered, washed with water and dried at 100° C. to constant weight. Elemental analysis of this product yielded 23.7% ruthenium, 44.4% carbon and 1.84% hydrogen. This corresponds to the formula $Ru(C_8H_4O_4)_2$; theoretically 23.5% Ru, 44.7% C and 1.73% H. The course of the reaction may have involved air oxidation of ruthenium from the (III) to the (IV) valence state, inasmuch as these valence states are very close energetically.

Samples of the prepared ruthenium terephthalate were compacted into flat plates of 10 mils in thickness and 3.5 cms radius at room temperature between polished steel plates at 20,000 psi in a laboratory press. Volume resistivity was determined using an Associated Research, Inc. Model 2850 megohm bridge. The volume resistivity of ruthenium terephthalate samples was on the order of 100 to 200 ohm-cms. Upon irradiation at a range of about 4 inches with a 150 watt near-UV and visible source, Philips "Agro-Lite", the volume resistivity dropped to 20–40 ohm-cms, indicating that the semiconductance of ruthenium terephthalate is light sensitive. The dielectric constant of the compound was too high to be measured by a capacitance bridge and this is indicative of the semiconductive properties of the compound.

For comparative purposes, typical metal terephthalates having high volume resistivities of $10^{12}$ to $10^{14}$ ohm-cm and dielectric constants of between 4 and 5 were tested. These values are given by Ca, Zn, Mg, Al, In, Pb, Cd, Sn(II), Fe(III), Sr, Hg, Co, Ni and Cu(II) terephthalates. Surprisingly, therefore, ruthenium terephthalate has an unusually high dielectric constant and is an excellent semiconductor in comparison to other metal terephthalate salts.

What is claimed is:
1. Ruthenium terephthalate.

* * * * *